US00PP14452P39

(12) United States Plant Patent
Peterson

(10) Patent No.: US PP14,452 P3
(45) Date of Patent: Jan. 13, 2004

(54) PAWPAW TREE NAMED 'WANSEVWAN'

(50) Latin Name: *Asimina triloba (L.) Dunal*
Varietal Denomination: Wansevwan

(76) Inventor: Robert Neal Peterson, P.O. Box 1277, Franklin, WV (US) 26807

( * ) Notice: Subject to any disclaimer, the term of this patent is extended or adjusted under 35 U.S.C. 154(b) by 0 days.

(21) Appl. No.: 09/954,536

(22) Filed: Sep. 18, 2001

(65) Prior Publication Data

US 2003/0056255 P1 Mar. 20, 2003

(51) Int. Cl.[7] ..... A01H 5/00
(52) U.S. Cl. ..... Plt./156

(58) Field of Search ..... Plt./156

*Primary Examiner*—Bruce R. Campell
*Assistant Examiner*—Susan B. McCormick

(57) ABSTRACT

Disclosed herein is a new and distinct variety of pawpaw tree, which has been given the name 'Wansevwan.' This variety is distinguished by good yields, atypical of pawpaw, and by its excellent fruit quality. Fruit are large with a low seed-to-fruit ratio, and possess the finest flavor found in pawpaws to date. The texture is melting, yet firmer than average which may help in shipping and handling. The number of fruit per cluster is low, often in singles, which simplifies harvesting. This variety is one of three varieties newly identified as having potential to establish a commercial pawpaw industry.

8 Drawing Sheets

BACKGROUND OF THE INVENTION

The present invention relates to a new and distinct and superior variety of the pawpaw which is of interest for its fruit.

The species—*Asimina triloba* (L.) Dunal—is the largest native edible fruit of North America, a member of the Annonaceae family, and thus a relative of the cherimoya, sweetsop, guanabana and custard apple (*Annona cherimola, A. squamosa, A. muricata* and *A. reticulata*), all of which are popular fruits that are widely cultivated in tropical and subtropical regions of the world, including southern Florida and southern California. The pawpaw is the only truly temperate member of the Annonaceae, being indigenous to a region stretching from the Great Lakes to the Gulf Coastal Plain and from the Chesapeake Bay to the Great Plains.

Currently, the pawpaw is considered to be semi-domesticated. Native Americans casually cultivated the tree, as did the white settlers who displaced them. The selection, propagation and naming of pawpaw varieties from the wild has been practiced for more than a century, and the backyard cultivation of pawpaws for personal use is not uncommon in Appalachia and parts of the Midwest. Numerous unregistered, unpatented varieties are available in the mail-order nursery trade.

Commercial cultivation of pawpaw has not developed, however. The fruit is fragile and highly perishable, which makes transport difficult. And scientific attention towards improving the fruit, its culture and its post-harvest handling has been neglected until recently. The lack of high quality cultivars that meet the requirements of producers and consumers is the foremost reason that commercial cultivation has not been undertaken.

The present invention, named 'Wansevwan,' by the developer, is one of three new and distinct varieties of pawpaw pawpaw, each of which represents a great improvement over existing pawpaw varieties because of higher yields, superior flavor, fewer seeds and firmer flesh. The other two varieties are 'Aidfievate', which is the subject of co-pending application Ser. No. 09/954,140, and 'Levfiv', which is the subject of co-pending application Ser. No. 09/954,186. These varieties possess the minimum overall qualities required for the development of a commercial pawpaw industry. The primary use of this pawpaw variety will be for fresh eating as a dessert fruit. Secondary use will be in processed products such as ice cream, yogurt, juice and cosmetics. Of the three, the variety 'Wansevwan' is outstanding for flavor, having the finest flavor found in pawpaws to date.

ORIGIN

The variety 'Wansevwan' was developed by R. Neal Peterson as the result of a breeding project to improve the pawpaw, which he began in 1980. The project was conducted during a period when Peterson was employed as an economist with the United States Department of Agriculture in Washington, D.C. However, because Peterson was not employed in any capacity as an horticulturist or other researcher in the biological sciences, and no Department of Agriculture plant stock, facilities or information were used, the United States government has no interest in the rights to the claimed variety.

The germplasm for Peterson's breeding project came principally from the surviving remnants of five historic collections of pawpaw dating to the early twentieth century that were the work of the most prominent pawpaw collectors and breeders of the time, and whose named material was no longer propagated or otherwise available. In 1982 germ plasm [open-pollinated seed] was collected from these remnants and included with open-pollinated seed from named cultivars, which became the germ plasm for his own breeding and selection work.

In 1983, the seed was germinated and the following spring 808 accessions were planted at the University of Maryland experiment station, the Wye Research & Education Center, Queenstown, Md. Since then, the orchard has been supervised by the inventor, with basic staff support from the university. Basic tasks such as fertilizing, spraying and mowing were conducted by the station staff. The inventor pruned, weeded, and collected data on growth rates, flowering, fruit set, yields, cluster size, fruit size and fruit quality, including data from taste panels which he organized.

In 1991, the inventor analyzed four years of data, and identified eleven trees as superior for further study. Nine of these cultivars are involved in regional variety trials around the country and have been termed advanced numbered selections. After nine additional years of observation, the original nine cultivars were narrowed to three that are consistently of the highest quality. One of these three bears the accession number PPF 1-7-1, and is the variety that is the subject of this application. This new variety, named 'Wansevwan,' originated as an open-pollinated seedling from the variety 'Overleese' which is an unregistered, unpatented cultivar originating circa 1950 near Rushville, Ind., and which is generally regarded as the standard pawpaw variety among knowledgeable pawpaw growers. The original tree PPF 1-7-1 is 18 years old.

ASEXUAL REPRODUCTION OF THE VARIETY

In 1994, the inventor began topworking the Wye orchard to his eleven advanced numbered selections, plus other already named varieties. Topworking was accomplished using bark-inlay grafting and chip-budding. Grafting of 'Wansevwan' was easily accomplished, by established methods, and gave a high percentage of takes. Replicates of 'Wansevwan' now number more than 20 at the Wye, having been propagated through successive cycles of grafting over seven years. The rootstock for these grafts were mature seedling pawpaw trees growing in the orchard, and were a portion of the original accessions from 1983, described previously. Eight grafted trees of 'Wansevwan' have been bearing fruit since 1996 and demonstrate that asexual reproduction of this new and distinct variety preserves the desirable characteristics of the variety and establishes and stably transmits those characteristics through successive propagation at the Queenstown location.

SUMMARY OF THE VARIETY

'Wansevwan' exceeds its parent variety 'Overleese' in vigor, yields, fleshiness, flavor and in having fewer fruits per cluster. The fruit is large, on average 260 gm for well-pollinated fruit, and may exceed 350 gm. It is usually borne in clusters of one, two or three. The fruit skin is thin to medium-thin and is thus slightly thicker than typical for the species. Skin color is pale green and very glaucous, and does not exhibit any reliable color break at ripeness. The fruit shape is ovoid-ovate and the dorsal side of the fruit [opposite the ventral suture] is usually slightly flattened. The composition is fleshy, with many fewer seeds relative to fruit weight than is typical of even the better named varieties. The aroma of the fruit before and after cutting is pleasant, neither too faint nor too pronounced. The flavor is excellent—mild, sweet, free of bitterness or astringency, with a pleasant aftertaste. The pungent asiminous component that is uniquely pawpaw and that many people find objectionable is noticeably weak. The flesh is firmer than average, very custardy and melting, with a pleasant mouth-feel and with no detectable fiber or grit. The ripening period at Queenstown has been mid to late season, September 10 to 24, more or less, depending on the degree of heat in the preceding months.

Non-fruit characteristic of 'Wansevwan' do not reliably distinguish it from other pawpaws. The leaf's color, shape, size and petiole are typical of the species. The aspect of the leaf in full sun is drooping in the same manner as other pawpaws. Neither do trunk, bark nor branching habit distinguish it. Flower measurements when taken as a whole may serve to identify 'Wansevwan', though perhaps not uniquely. Its flower is slightly smaller than average, more tightly closed than typical in the female stage, and more widely flaring than typical in the male stage. For exact data, see the detailed description and accompanying photographs.

This variety is susceptible to *Talponia plummeriana*, the pawpaw peduncle moth, and to *Eurytides marcellus*, the zebra swallowtail butterfly, the same as for the species. This variety is believed to be susceptible to pawpaw decline disease but this remains unconfirmed. This variety does not require pruning but does respond well to pruning, forming a broadly spreading tree of globular shape with wide crotch angles. Pruning has an invigorating effect that stimulates growth and bearing. Corrective pruning is minimal.

BRIEF DESCRIPTION OF THE DRAWINGS

In the accompanying drawings, leaves, flowers, fruits and seeds are shown in color that is as nearly true as is reasonably possible in color photographs of this nature. The deep maroon hues of the flowers are the most difficult for photoemulsions to render accurately.

BOTANICAL DESCRIPTION

Figure 1:
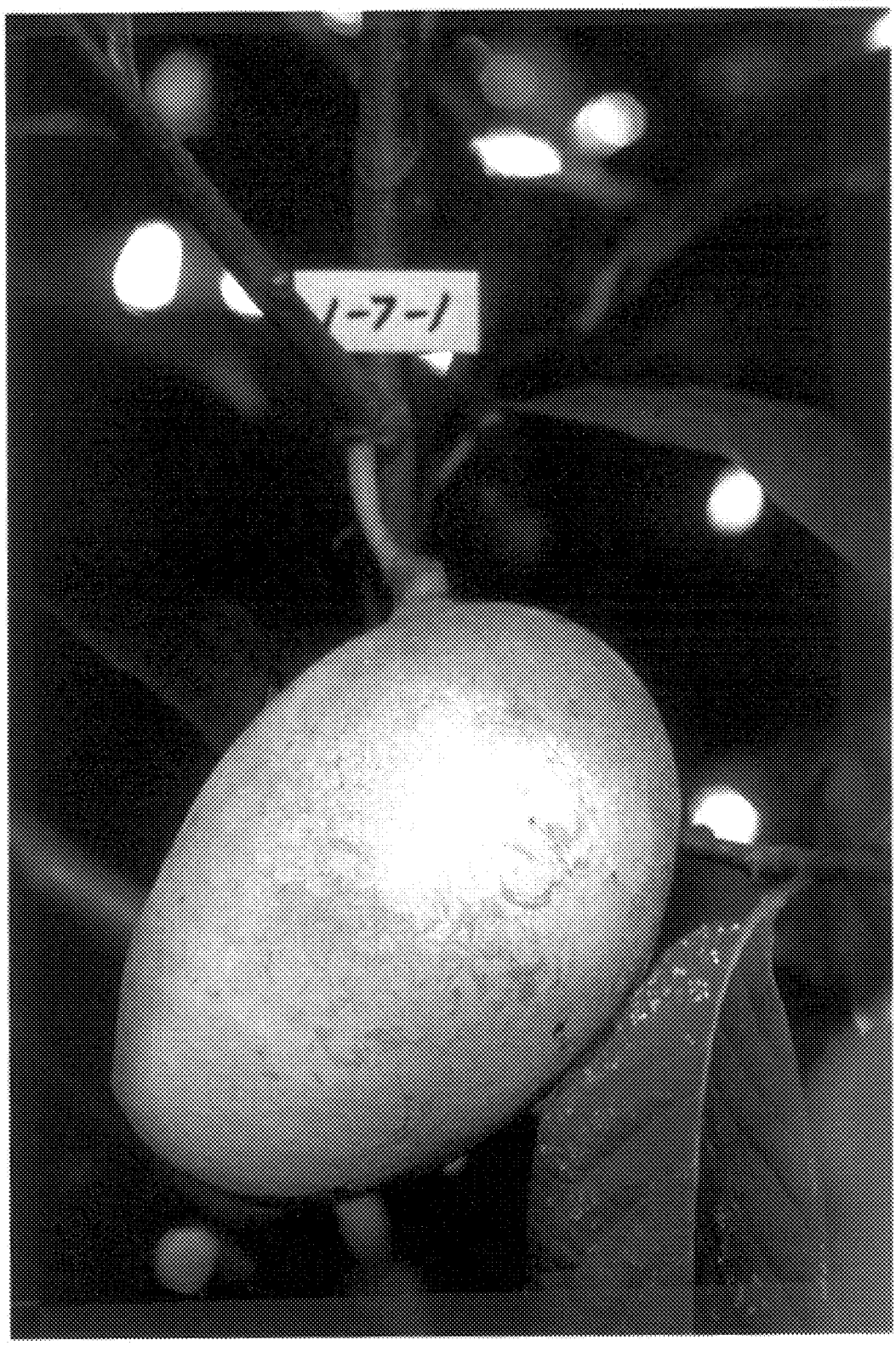
FIG. 1 Shows the fruit of the new variety, hanging on the tree.
Figure 2:
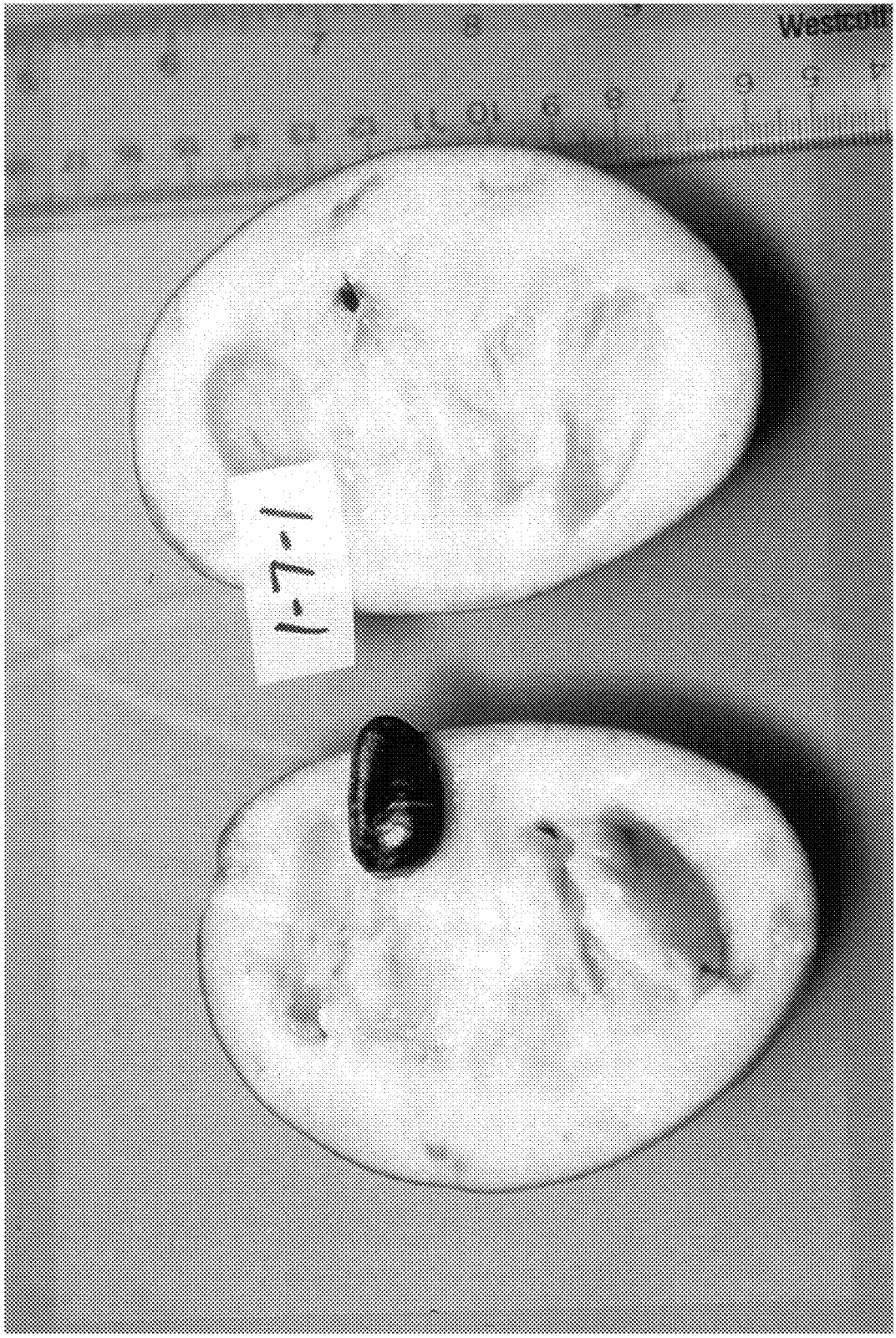
FIG. 2 Shows the fruit of the new variety in dissection, revealing the color, fleshiness and seeds.
Figure 3A:
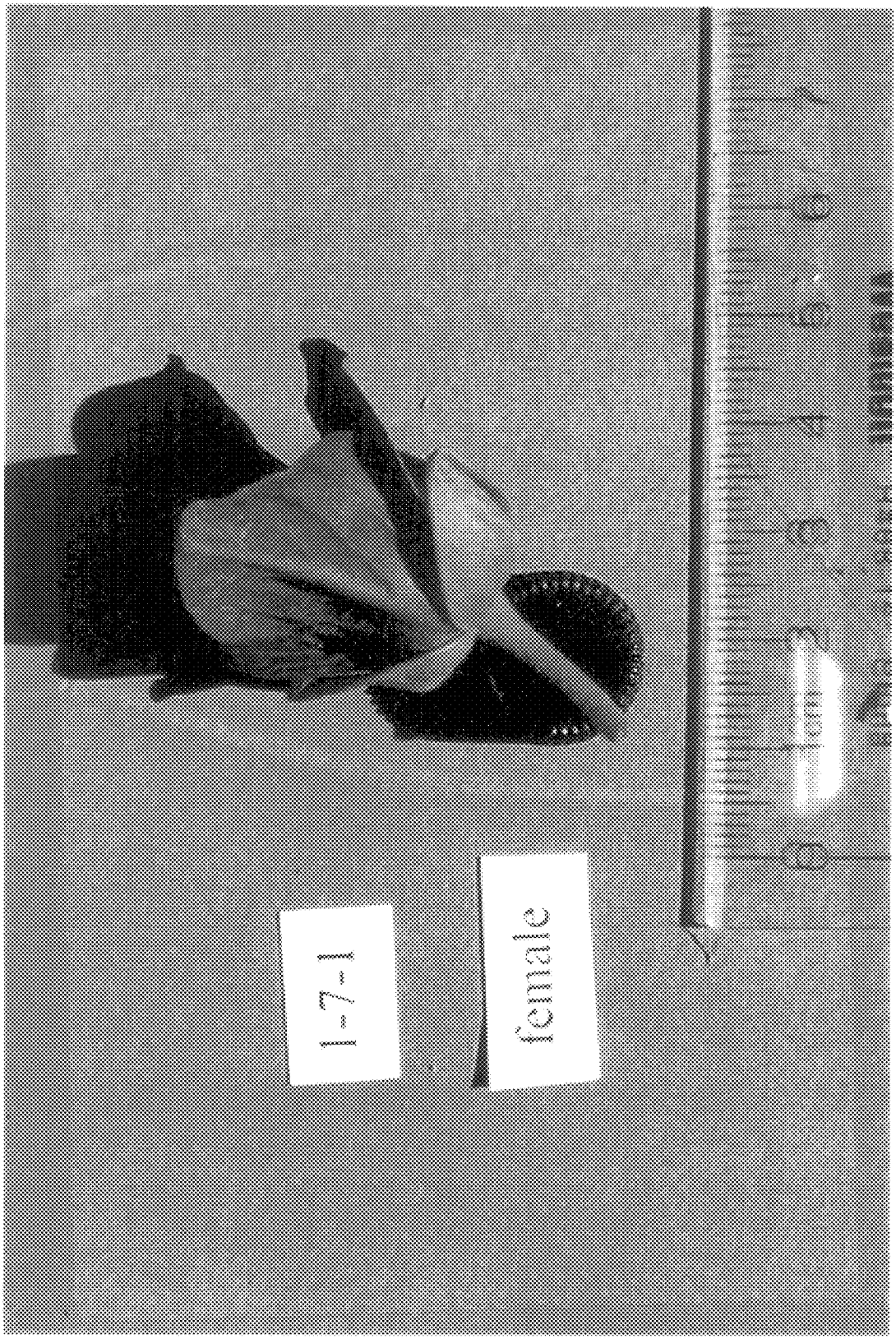
FIG. 3 Shows the flower of the new variety in the female stage, in profile and dissection.
Figure 3B:
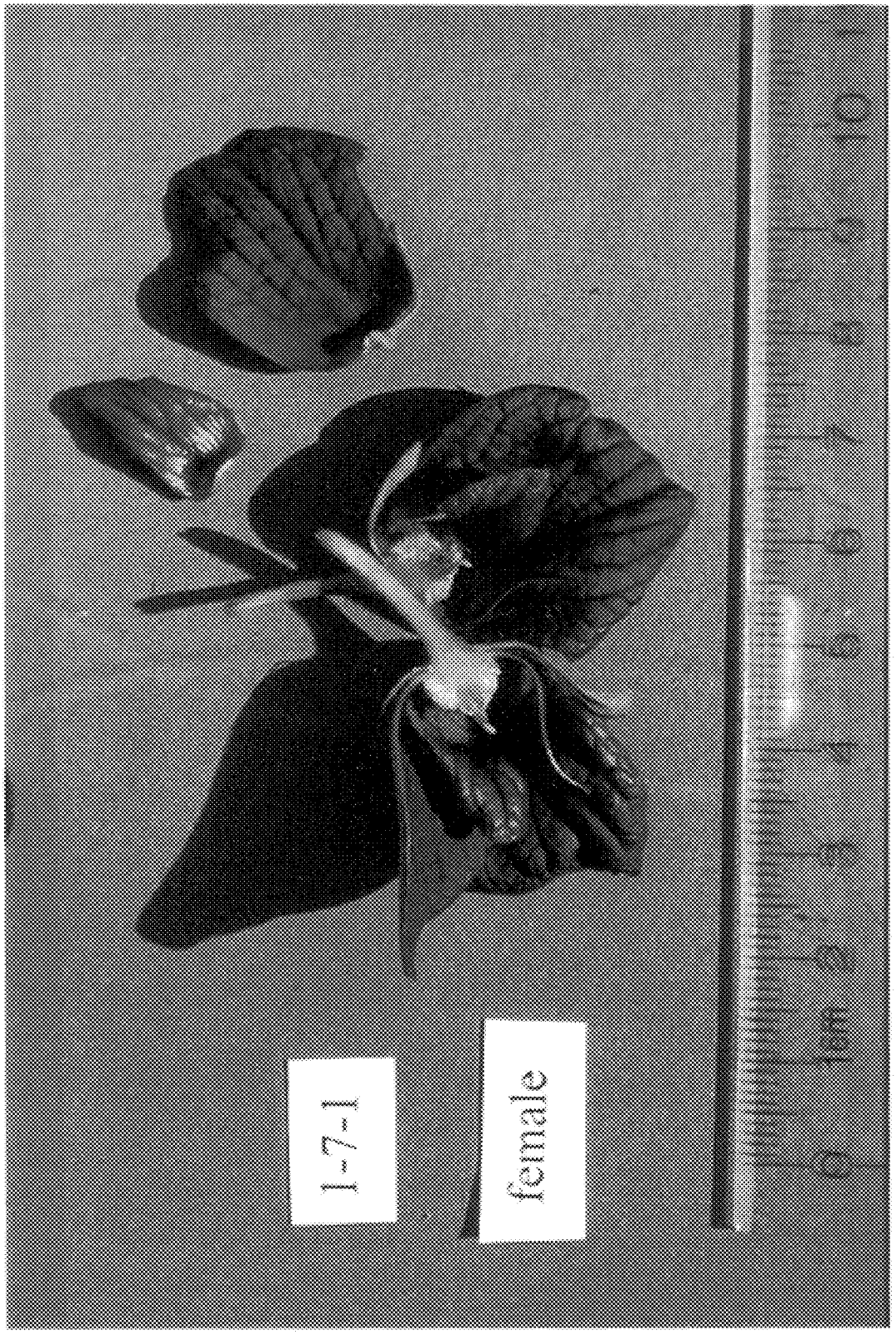
Figure 4A:
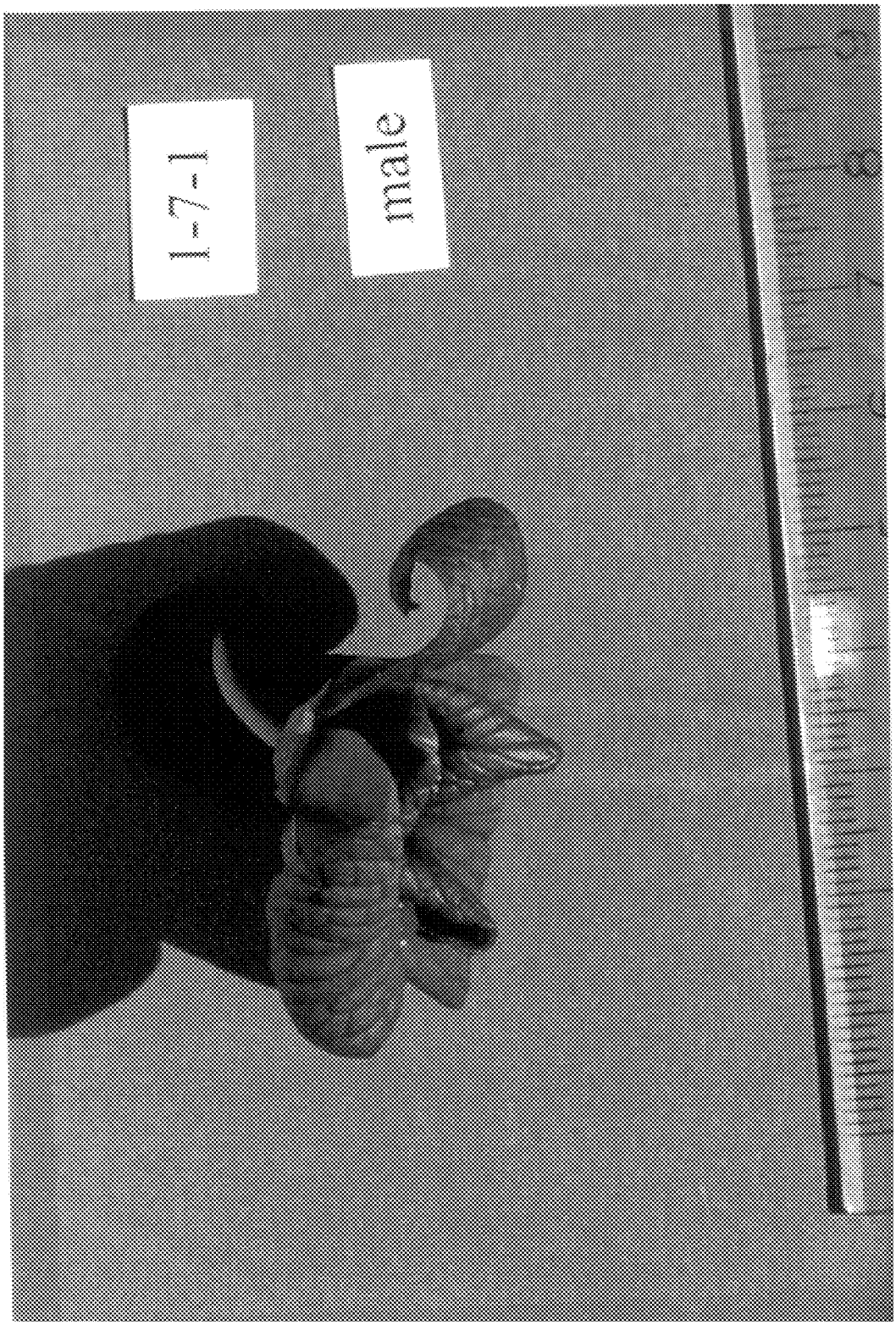
FIG. 4 Shows the flowers of the new variety in the male stage, in profile and dissection.
Figure 4B:
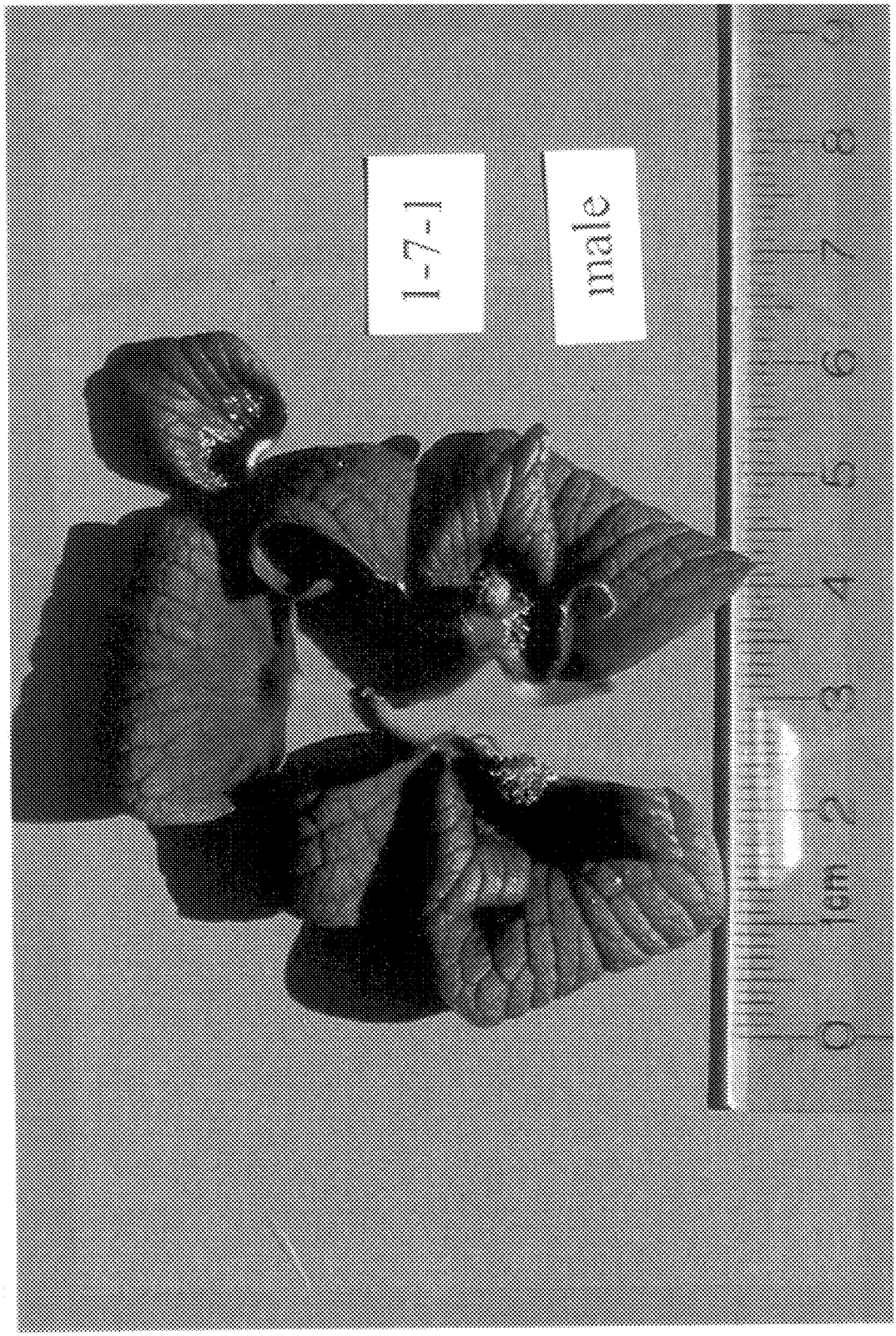
Figure 5:
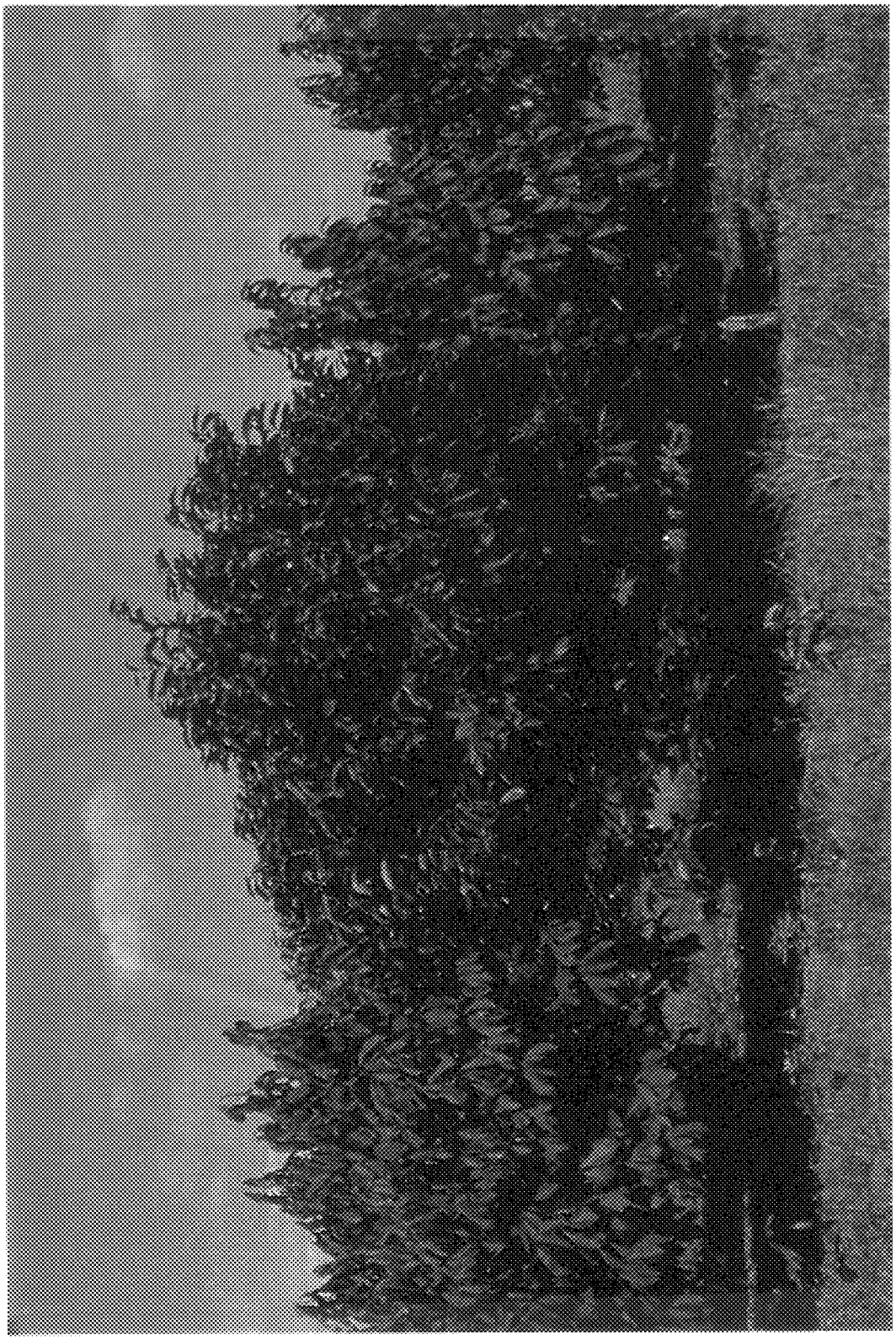
FIG. 5 Shows the habit of a pruned tree of the new variety.
Figure 6:
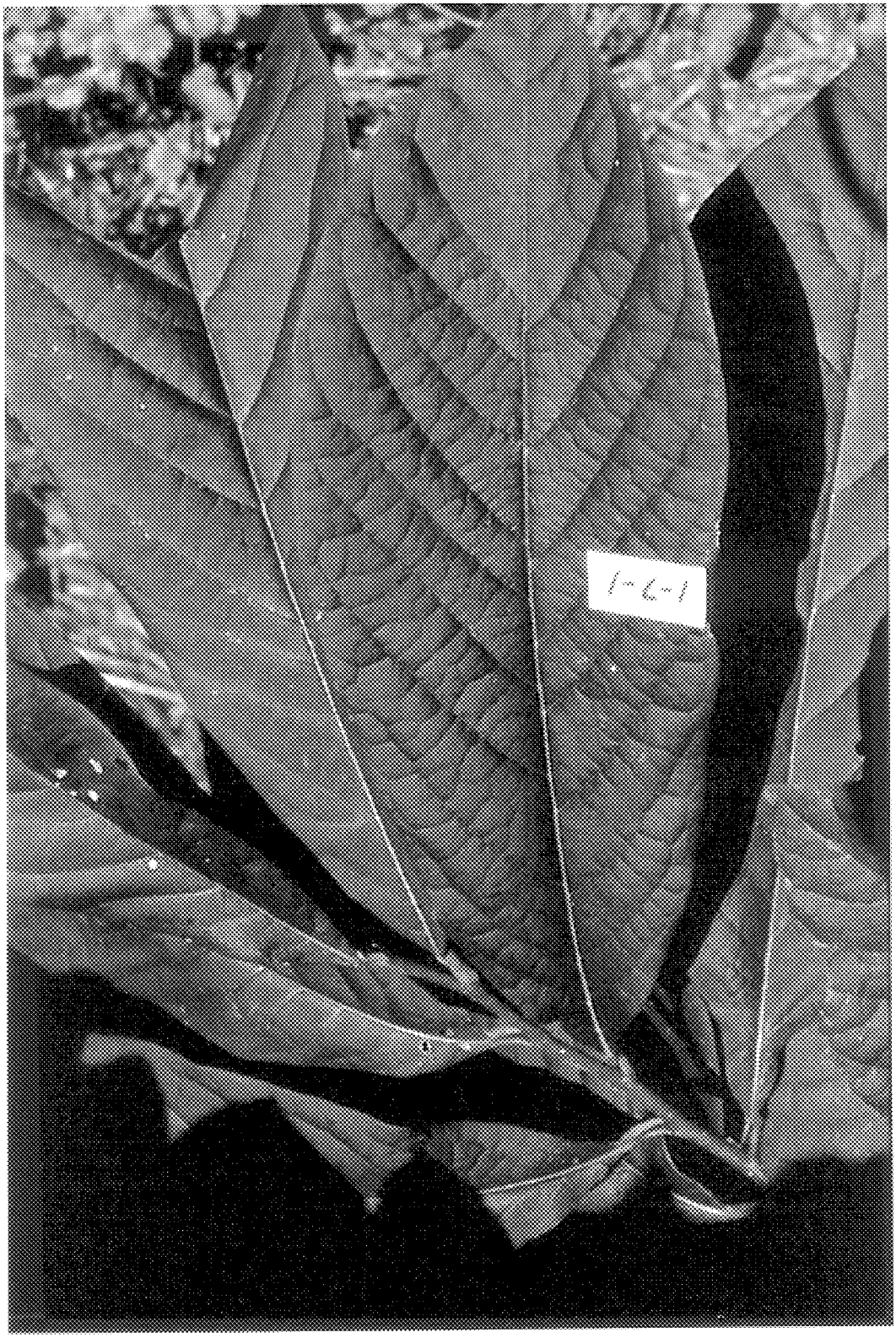
FIG. 6 Shows a close-up of the leaves of the new variety.

Because no variety of *Asimina triloba* has ever before been patented, we include a botanical description of the species drawn from two taxonomic authorities, C. S. Sargent and R. Kral.

Shrub or small tree 1.5–11 (~14) m tall from a stout, sometimes branched taproot, with a straight trunk seldom exceeding 30 cm in diameter; the bark of older trees gray-brown, shallowly furrowed, and marked with large ash-colored blotches; that of new shoots moderately to copiously dark brown-hairy toward the summit, aging smooth, gray-brown, winter vegetative buds naked, without stipules, acuminate and dark brown to rusty brown-hairy, 2–5 mm long, and tightly appressed against the stem; winter flower buds globose, dark brown-hairy, 2.5–5 mm in diameter; leaves membranaceous, oblong-obovate to oblanceolate, 15–30 cm long; apex acute to acuminate; base more or less gradually attenuate to the short (0.5–1 cm) petiole; margin flat or scarcely revolute; young surfaces sparsely appressed reddish-pubescent above; densely so beneath, becoming glabrous above and sparsely hairy on the veins beneath; flowers green initially, then turning brown to maroon to deep vinous red, 2–5 cm broad with a faintly fetid aroma, on densely dark brown-hairy, nodding peduncles 1–2.5 cm long which develop from the axils of the prominent leaf scars; calyx 8–12 mm long, of three triangular-deltoid sepals which are striate with brown hairs on the outside, glabrous within; outer petals 1.5–2.5 cm long, oblong-elliptic, with ascending bases and slightly to conspicuously recurved tips, copiously appressed-hairy along the veins outside, glabrous and impressed-veiny within; inner petals ⅓–½ the length of the outer, elliptic, saccate-based, recurved tipped, glabrate without, glabrous and impressed-veiny within, with a corrugated nectary zone usually of a lighter color; androecium globular, 0.5–1 cm broad, pale green at anthesis; gynoecium of 3–10 fusiform appressed-red-hairy carpels; fruits oblong-cylindric, 5–15 cm long, yellow-green to brownish when ripe, attached obliquely to the enlarged torus of the peduncle in clusters of variable number; seeds 1.5–2.5 cm long, brown to castaneous, shiny when mature, bean-shaped, somewhat laterally compressed, contained within an aril that is confluent with the pericarp from which the seed readily separates.

DETAILED DESCRIPTION OF THE INVENTION

Following is a detailed description of the new variety of pawpaw tree with color terminology in accordance with The Royal Horticulture Society (R.H.S.) Colour Chart (Ed. No. 2, 1986) except where general color terms of ordinary dictionary significance are used.

Tree:

*Size.*—Small. 3.5 m on its own roots but taller on more vigorous rootstock.

*Vigor.*—Medium when grafted to other rootstock. Approximately 50 cm growth on strong primary laterals under standard fertilization of 50 lbs of N per acre.

*Habit.*—Rounded with age.

*Branching pattern.*—Spreading with time, and more so with pruning. Wide crotch angles and branches widely spaced. On vigorously growing leaders, a ladder-like formation may form, consisting of small horizontal branches (5–10 cm long) that ascend in regular alternating fashion on both sides of the leader.

*Apical dominance.*—Medium.

*Trunk.*—Diameter 9.5 cm measured at 30 cm above ground level.

*Bark.*—Smooth with small raised horizontal lenticels, typical of the species. Color R.H.S. Grey 201B on both trunk and branches.

Leaf buds:

*Length.*—Axillary buds growing on branches of normal vigor, 3.4 mm average with a range of 3.2 to 3.5 mm. Buds growing on branches of high vigor larger, 4.7 mm average with a range of 4.5 to 4.9 mm.

Leaves:

*Shape.*—Oblanceolate with acuminate tip and attenuate to the base, as is typical for the species. Average ratio of width to length is 0.435.

*Size.*—Measurements are from mature leaves attached at midpoint of actively growing shoots of current season's growth. Average size is 11.1 cm wide, 25.5 cm long.

*Color.*—Upper surface varies between R.H.S. Green 139A and Yellow-Green 147A. Lower surface R.H.S. Yellow-Green 146A. Both colors typical for the species.

*Aspect.*—Drooping when grown in full sun, as is typical for the species.

*Margin.*—Entire.

*Texture.*—Smooth to very slightly impressed veiny, typical for the species.

*Arrangement.*—Alternate opposite.

*Petiole.*—Color yellow-green similar to lower leaf surface. Average diameter 3.3 mm at the petiole midpoint. Length ranges from 13.0 to 15.4 mm with an average of 14.2 mm. NOTE: The structure of the leaf lamina is such, in the way that it tapers gradually to the petiole, that visual demarcation of the petiole terminus is imprecise and the resultant measurement of petiole length has a high margin of error. The measurements reported here are based on a precise tactile method. By means of running the back of one's thumbnail down the midvein (on the underside of the leaf) towards the petiole one encounters a sudden change in curvature, diameter, and hardness. This point of change is the petiole terminus and is easy to detect and replicate.

Flower buds:

*Size.*—Length 5.5 mm average. Width 3.9 mm average.

*Appearance.*—Very dark brown, between R.H.S. Brown 200A and Black 202A. Surface densely pubescent, velvety.

Flower:

*Size.*—Small to average. As the flower matures from female to male stage, the petals reflex, and therefore measured flower size is specific to flower stage, which data are presented below.

*Outer petals.*—Average of 22 mm wide, 26 mm long. Average ratio of width to length 0.85.

*Inner petals.*—Average of 9 mm wide, 15 mm long. Average ratio of width to length 0.60.

*Color.*—Maroon.

*Form of female stage flower.*—More tightly closed than average.

*Size of the female stage flower.*—Diameter 37 mm average.

*Nectary band of female stage flower.*—Color is ivory.

*Form of male stage flower.*—More widely flaring than average, and outer petals more recurved than typical.

*Size of the male stage flower.*—Diameter 47 mm average.

*Nectary band of male stage flower.*—Color is deep maroon, basically indistinguishable from the inner petal color.

*Peduncle.*—Length 16 mm average. Lightly pubescent with brown hairs.

Fruit:

*Dates of picking.*—Mid to late season, generally from September 10 to 24 at Queenstown, but dates can vary more than a week depending on the degree of summer heat.

*Cluster size.*—Few fruited. One- and two-fruited clusters are prevalent, and this small cluster size is atypical of pawpaw. Larger clusters occur, however, even exceeding five fruits. Within large clusters the fruit size typically varies greatly; the range of size not uncommonly exceeding 2-to-1. High within-cluster variance of fruit size is common in most pawpaw varieties.

*Fruit shape.*—Ovoid-ovate often with a slight flattening of the dorsal surface. Shape varies considerably; but large well-formed fruit in single-fruited cluster tend towards length-to-width-to-depth proportions of 100:70:65.

*Fruit size.*—Large, 260 gm average for well-pollinated fruit. Much larger than typical pawpaw. Size varies from small (~33 gm) to very large (~350 gm), dependent on the number of fertilized seed present in the fruit. Lengths normally range 5.0–12.3 cm, widths 3.5–8.6 cm, and depths 3.3–8.0 cm.

*Suture.*—Not prominent. Fine green or grey line, often indistinct and discontinuous, or occasionally a pale yellow stripe.

*Abscission type.*—Primary mode is for fruit to abscise from the torus of the peduncle.

*Abscission scar.*—Small, 6.4 mm in diameter. A character of low variance.

*Peduncle.*—Length 14.3 mm on average, ranging from 12.8 to 15.8 mm, but longer (up to 20 mm) on vigorous trees. Diameter extremely variable, varying in proportion to the cluster fruit mass, as is typical of the species. However, in comparison to the range of peduncle sizes of pawpaw cultivars, and relative to the total cluster fruit weight, the diameter is thin. Peduncle pubescence dark brown to rufus, usually sparse, sometimes nearly glabrous. The point of peduncle attachment to single-fruited clusters is offset greatly from the central axis of the fruit, on the dorsal side of the fruit.

*Skin color.*—Under-ripe fruit pale green and very glaucous, R.H.S. Yellow-Green 147D. Ripe fruit pale yellowish green and very glaucous, R.H.S. Yellow-Green 145A. After the fruit passes its climacteric peak and falls from the tree, brown blotches appear which spread to cover the entire skin surface, as is typical for the species.

*Color break.*—Not reliable. Above noted color change too subtle and not reliably present to be a dependable guide to picking.

*Skin thickness.*—Medium-thin.

*Aril.*—Thin, tender, and edible.

*Fleshiness.*—High. Percent seed is 5.4 on average. The average quantity of pulp per seed is 26.1 gm.

*Flesh color.*—Creamy yellow and uniform throughout. R.H.S. Yellow 12C.

*Aroma of uncut fruit.*—Pleasant. Medium power.

*Aroma of cut fruit.*—Pleasant. Medium power.

*Flavor.*—Very sweet, Brix 18%, mild, non-bitter, and non-astrigent. Pungent asiminous component low.

*Aftertaste.*—Pleasant, long lingering, no negative components.

*Consistency.*—Very pleasant mouth-feel. Flesh is slightly firmer than typical pawpaw, but melting in the mouth, with a very smooth, custardy texture. No detectable fiber or grit.

*Use.*—Principally for fresh eating as a dessert fruit. Secondarily in processed products.

Seed:

*Size.*—Large. 1.80 gm average weight. Dimensions 26.1 mm long, 14.6 mm wide, 7.9 thick on average.

*Color.*—Dark brown. R.H.S. Brown 200A.

*Number per fruit.*—8 per an average fruit of 260 gm. As fruit size varies greatly in pawpaw (including this new variety) the seed number per fruit is not a stable character, unlike the seed-to-fruit ratio (percent seed) which is stable.

Physiological and ecological characters:

*Graftability.*—Very easy to graft by virtually all methods. Percent take is medium for pawpaw, in vicinity of 75%.

*Habit of tree after grafting.*—Moderately invigorated. It appears that common seedling rootstocks have more vigor than the mother tree's own roots.

*Pruning.*—The tree responds very well to pruning, without overly vigorous vegetative response. Flowering and general vigor improved by pruning.

*Flower count.*—Medium to high. Average of 4.2 blossoms per branch on vigorous branches, but flower number varies considerably depending on the vigor of the branch.

*Self-fruitfulness.*—Requires cross pollination.

*Bearing.*—Annual and consistent.

*Fruit set.*—Low, less than 20 percent.

*Yields.*—High. From mature trees approximately 30 lbs. of fruit per tree. At orchard densities of 330 trees per acre, this is 10,000 lbs per acre.

*Keeping quality of fruit (normal storage, 24° C.).*—Short. Three days when ripe. Typical for the species.

*Keeping quality of fruit (cold storage, 2° C.).*—Moderate. Three weeks when picked under-ripe.

*Shipping quality of fruit.*—Medium if shipped refrigerated with adequate cushioning. Poor otherwise because of the rapid ripening, which is typical for the species.

*Drought and heat tolerance.*—Good, similar to the species. Drought tolerance superior to peach.

*Hardiness.*—Fully hardy at Queenstown location, USDA Zone 7. Believed hardy to Zone 5 (average annual minimum temperature −30° C.), the same as for the species.

*Resistance to Talponia plummeriana.*—Susceptible.

*Resistance to Eurytides marcellus.*—Susceptible.

*Resistance to pawpaw decline disease.*—Believed to be susceptible.

Variance in botanical details: The pawpaw tree and its fruit described herein will vary due to climate, soils, growing conditions and culture.

I claim:

1. A new and distinct variety of pawpaw tree obtained as an open-pollinated seedling of 'Overleese' (unpatented), substantially as shown and described herein.

* * * * *